United States Patent

Perronnet et al.

[11] 4,000,298
[45] Dec. 28, 1976

[54] NOVEL FUNGICIDAL COMPOSITION AND METHOD USING BENZIMIDAZOLE DERIVATIVES

[75] Inventors: Jacques Perronnet; Pierre Girault, both of Paris, France

[73] Assignee: Roussel-UCLAF, Paris, France

[22] Filed: Oct. 30, 1975

[21] Appl. No.: 627,276

Related U.S. Application Data

[62] Division of Ser. No. 398,416, Sept. 18, 1973, Pat. No. 3,932,447.

[30] Foreign Application Priority Data

Sept. 27, 1972 France .......................... 72.34135

[52] U.S. Cl. ............................... 424/273
[51] Int. Cl.² ............................ A01N 9/22
[58] Field of Search .......................... 424/273

[56] References Cited

UNITED STATES PATENTS

| 3,541,213 | 11/1970 | Klopping | 424/273 |
| 3,626,070 | 12/1971 | Soboczenski | 424/273 |

Primary Examiner—Albert T. Meyers
Assistant Examiner—Allen J. Robinson
Attorney, Agent, or Firm—Hammond & Littell

[57] ABSTRACT

Novel benzimidazole derivatives of the formula

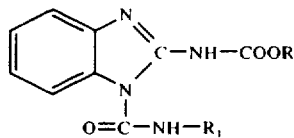

wherein R is alkyl of 1 to 2 carbon atoms and $R_1$ is selected from the group consisting of tetrahydrofurfuryl, a saturated or unsaturated oxygen heterocycle of 4 to 5 carbon atoms and

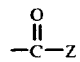

wherein Z is unsaturated hydrocarbon radical of 2 to 4 carbon atoms having at least 2 halogen atoms which possess fungicidal activity.

6 Claims, No Drawings

NOVEL FUNGICIDAL COMPOSITION AND METHOD USING BENZIMIDAZOLE DERIVATIVES

PRIOR APPLICATION

This application is a division of our copending, commonly assigned U.S. application Ser. No. 398,416 filed Sept. 18, 1973, now U.S. Pat. No. 3,932,447.

OBJECTS OF THE INVENTION

It is an object of the invention to provide the novel benzimidazole derivatives of formula 1 and a process for their preparation.

It is another object of the invention to provide novel fungicidal compositions.

It is another object of the invention to provide a novel method of killing fungi.

These and other objects and advantages of the invention will become obvious from the following detailed description.

THE INVENTION

The novel benzimidazole derivatives of the invention have the formula

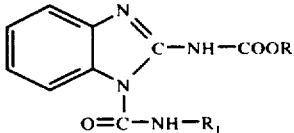

I wherein R is alkyl of 1 to 2 carbon atoms and $R_1$ is selected from the group consisting of tetrahydrofurfuryl, a saturated or unsaturated oxygen heterocycle of 4 to 5 carbon atoms and

wherein Z is unsaturated hydrocarbon radical of 2 to 4 carbon atom having at least 2 halogen atoms.

Examples of $R_1$ are heterocycles such as tetrahydrofurfuryl, furanyl, pyranyl, dihydropyranyl, tetrahydrofuranyl and tetrahydropyranyl and unsaturated acyl groups such as $\beta,\beta$-dichlorovinylcarbonyl and $\alpha,\beta,\beta$-trichlorovinylcarbonyl, R is methyl or ethyl.

The compounds of formula I can be prepared by reacting a compound of the formula

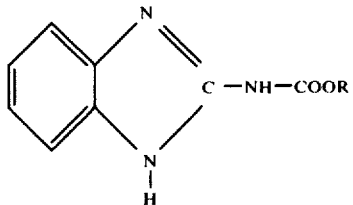

II with an isocyanate of the formula

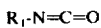

III wherein R and $R_1$ have the above definitions to obtain the corresponding compound of formula I. The condensation is preferably effected in an organic solvent such as tetrahydrofuran in the presence of an organic base such as 1,4-diazabicyclo (2,2,2) octane.

The 2-benzimidazole carbamic acid esters of formula II can be prepared by the process described in U.S. Pat. No. 2,933,504 and the isocyanates of formula III can be prepared by known methods.

The novel fungicidal compositions of the invention contain as the active ingredient at least one compound of formula I and may contain one or more other pesticidal agents. The compositions may be in the form of powders, suspensions, emulsions or solutions containing, besides the active ingredients, non-ionic, cationic or anionic surface active agents; inert powders such as talc, clays, silicates, Kieselguhr; or a vehicle such as water, alcohols, hydrocarbons or other organic solvents, mineral, animal or vegetable oils, etc.

The fungicidal compositions preferably contain 25 to 95% by weight of the active compound when a powder for foliar spraying or 2.5 to 99% by weight of active compound when a powder for foliar dusting. An example of fungicidal composition in the form of a wettable powder is 25% by weight of methyl 1-[3'-(5',6'-dihydropyranyl)]-carbamoyl-2-benzimidazolyl-carbamate, 15% by weight of Ekapersol S (condensation product of sodium naphthalenesulfonate), 0.5% by weight of Brecolane NVA (sodium alkylnaphthalenesulfonate), 34.5% by weight of Zeosil 39 (precipitated synthetic hydrated silica) and 25% by weight of Vercoryl S (colloidal kaolin).

The novel method of the invention for killing fungi comprises contacting the fungi with a fungicidally effective amount of at least one compound of formula I.

In the following examples there are described several preferred embodiments to illustrate the invention. However, it should be understood that the invention is not intended to be limited to the specific embodiments.

EXAMPLE 1

Methyl-1-(4'-tetrahydropyranyl)-carbamoyl-2-benzimidazolyl-carbamate

STEP A: 4-tetrahydropyranyl-isocyanate

A solution of 121.6 g of 4-tetrahydropyranyl carboxylic acid chloride [J. Pharm. Pharmac., Vol. 15 (1963) p. 167] in 250 ml of toluene was added dropwise at 10° C to 60 g of sodium nitride in 150 ml of distilled water and the mixture was stirred for 2 hours. The organic phase was recovered by decantation, was washed with a sodium bicarbonate solution, then with water and dried. The organic solution was heated at 100° C for 2¾ hours in the presence of m-dinitrobenzene and heating was continued until gas evolution ceased. The solution was concentrated under reduced pressure and the residual oil was distilled to obtain 83.6 g of 4-tetrahydropyranyl-isocyanate boiling at 79°–80° C under 23 mm Hg and having a refractive index $n_D^{20} = 1.4658$.

STEP B: Methyl 1-(4'-tetrahydropyranyl)-carbamoyl-2-benzimidazolyl-carbamate 35 g of 4-tetrahydropyranyl-isocyanate were added dropwise to a suspension of 38.4 g of methyl 2-benzimidazolyl-carbamate and 0.3 g of 1,4-diazbicyclo (2,2,2) octane in 600 ml of tetrahydrofuran and the mixture was stirred at 23° C for 5 hours. The mixture was filtered and the filtrate was evaporated to dryness under reduced pressure. The product was taken up in isopropyl ether and the crystals formed were recovered by vacuum filtration. This step was repeated 3 more times and the crystals were dried under reduced pressure at room temperature to obtain 59 g of methyl 1-(4'-tetrahydropyranyl)-carbamoyl-2-benzimidazolyl-carbamate in the form of a white solid decomposing at 252° C.

Analysis: $C_{15}H_{18}O_4N_4$ Calculated: %C, 56.59; %H, 5.69; %N, 17.6. Found: C, 55.1; H, 5.6; N; 17.7.

I.R. Spectrum: presence of carbonyl, aromatic ring, NH and NH/OH

EXAMPLE 2

Methyl 1-(2'-tetrahydropyranyl)-carbamoyl-2-benzimidazolyl-carbamate 30 ml of 2-tetrahydropyranyl-isocyanate were added to a suspension of 30 g of methyl 2-benzimidazolyl-carbamate in 600 ml of tetrahydrofuran and the mixture was stirred for 5 hours at room temperature and was then filtered. The filtrate was evaporated to dryness under reduced pressure and the residue was taken up in hexane. The mixture was vacuum filtered and the product was dried under reduced pressure to obtain 50 g of methyl 1-(2'-tetrahydropyranyl)-carbamoyl-2-benzimidazolyl-carbamate in the form of a white solid decomposing at 236° C.

Analysis: $C_5H_{18}N_4O_4$ Calculated: %C, 56.59; %H, 5.69; %N, 17.60. Found: C, 56.3; H, 5.5; N, 17.2.

I.R. Spectrum: presence of carbonyl, NH/OH, C=N and C—O—C

EXAMPLE 3

Methyl 1-[3'-(5',6'-dihydropyranyl)]-carbamoyl-2-benzimidazolyl-carbamate

STEP A: 3-)5,6-dihydropyranyl)-isocyanate

A solution of 61.5 g of sodium nitrite in 185 ml of distilled water stood for 16 hours at 0° C and then a solution of 119 g of 3-(5,6-dihydroyranyl)-carboxylic acid chloride in 370 ml of toluene was added dropwise thereto at 5° C. The mixture was stirred for 15 minutes and was decanted. The toluene phase was washed at 0° C with a 10% aqueous sodium carbonate solution, then with water and dried at 5° C. 2.14 g of m-dinitrobenzene were added and the mixture was heated at 130° C with stirring for 3 hours. After standing for 16 hours at 0° C, the mixture was distilled to obtain 20 g of 3-(5,6-dihydropyranyl)-isocyanate as a colorless oil boiling at 76° C under 16 mm Hg and having a refractive index $n_D^{20} = 1.4872$.

STEP B: Methyl 1-[3'-(5',6'-dihydropyranyl)]-carbamoyl-2-benzimidazolyl-carbamate 15 g of 3-(5,6-dihydropyranyl)-isocyanate were added to 20 g of methyl 2-benzimidazolyl-carbamate and 0.2 g of 1,4-diazabicylo (2,2,2) octane in 400 ml of tetrahydrofuran and the mixture was stirred for 17 hours at room temperature and then was filtered. The filtrate was evaporated to dryness under reduced pressure and the dry extract was taken up in isopropyl ether. The mixture was vacuum filtered and the precipitate was dried to obtain 9.8 g of methyl 1-[3'-(5',6'-dihydropyranyl)]-carbamoyl-2-benzimidazolyl-carbamate decomposing at 218° C.

Analysis: $C_{15}H_{16}N_4O_4$ Calculated: %C, 56.96; %H, 5.1; %N, 17.71; Found: C, 55.9; H, 5.3; N, 16.5;

EXAMPLE 4

Methyl 1-(2'-tetrahydrofurfuryl)-carbamoyl-2-benzimidazolyl-carbamate

STEP A: 2-tetrahydrofurfuryl-isocyanate 100 g of phosgene were dissolved by bubbling into 1250 ml of toluene and then 100 g of tetrahydrofurfurylamine and 0.2 g of dinitrobenzene were added dropwise at 12° C to the said solution. The mixture was refluxed for 5 hours while bubbling phosgene through it and was then evaporated to dryness. The residue was distilled to obtain 40.5 g of 2-tetrahydrofurfuryl-isocyanate as a colorless liquid boiling at 92°C under 30 mm Hg and having a refractive index $n_D^{23} = 1.4520$.

STEP B: Methyl 1-(2'-tetrahydrofurfuryl)-carbamoyl-2-benzimidazolyl-carbamate 30 g of 2-tetrahydrofurfuryl-isocyanate were added dropwise to a suspension of 30 g of methyl 2-benzimidazolyl-carbamate and 1 g of 1,4-diazabicyclo (2,2,2) octane in 300 ml of tetrahydrofuran and the mixture was stirred for 20 hours and vacuum filtered to obtain 19 g of the desired product melting with decomposition at 140° C. The filtrate was evaporated to dryness under reduced pressure and the residue was washed with isopropyl ether and dried. The product was purified by dissolution in chloroform and precipitation with hexane to obtain a second crop of methyl 1-(2'tetrahydrofurfuryl)-carbamoyl-2-benzimidazolyl-carbamate as a white solid decomposing at 140° C.

Analysis: $C_{15}H_{18}N_4O_4$ Calculated: %C, 56.6; %H, 5.7; %N, 17.6. Found: C, 56.3; H, 5.7; N, 17.6.

I.R. Spectrum: presence of carbonyl, C=N, NH and aromatic type bonds.

EXAMPLE 5

Methyl 1-trichloroacryloyl-carbamoyl-2-benzimidazolyl-carbamate

STEP A: Trichloroacryloyl-isocyanate 260 ml of oxalyl chloride were added to 225 g of trichloroacrylamide in 525 ml of dichloroethane cooled to 2° C and the mixture was held at 0° C for 1 hour and then refluxed for 16 hours. The resulting solution was evaporated under reduced pressure and the residue was distilled to obtain 232 g of trichloroacryloyl-isocyanate boiling at 86° C under 20 mm Hg and having a refractive index $n_D^{23} = 1.538$.

STEP B: Methyl 1-trichloroacryloylcarbamoyl-2-benzimidazolyl-carbamate 13.5 g of trichloroacryloyl-isocyanate were added dropwise to 10 g of methyl 2-benzimidzolyl-carbamate and 0.1 g of 1,4-diazabicylco (2,2,2) octane in 160 ml of tetrahydrofuran and the mixture was stirred for 17 hours at room temperature and was vacuum filtered. The crystals obtained were washed with petroleum ether and dried under reduced pressure to obtain 18.2 g of methyl 1-trichloroacryloylcarbamoyl-2-benzimidazolyl-carbamate as a solid melting at 231° C.

Analysis: $C_{13}H_9Cl_3N_4O_4$ Calculated: %C, 39.86; %H, 2.33; %N, 14.32; %Cl, 27.16. Found: C. 41.4; H, 3.1; N, 13.6; Cl 26.4.

I.R. Spectrum: presence of carbonyl, OH/NH, C=N and aromatic type bonds.

FUNGICIDAL ACTIVITY

A. Test against Botrytis cinerea (in liquid nutritive media)

0.5 ml of a suspension of spores of Botrytis cinerea and 0.5 ml of a suspension of the test product were added to 4 ml of a nutritive media based on oat meal and the readings were made after storage for 6 days at 24° C. The results of Table 1 are expressed as percent of efficacy as compared to untreated controls. Compound A is methyl 1-(4'-tetrahydropyranyl)-carbamoyl-2-benzimidazolyl-carbamate, compound B is methyl 1-(2'-tetrahydropyranyl)-carbamoyl-2-benzimidazolyl-carbamate and compound C is methyl 1-[3'-(5',6'-dihydropyranyl)]carbamoyl-2-benzimidazolyl-carbamate.

TABLE 1

| Compound | Concentration in ppm | | | | |
|---|---|---|---|---|---|
| | 40 | 20 | 10 | 5 | 1 |
| A | 100 | 100 | 100 | 100 | 100 |
| B | 100 | 100 | 100 | 100 | 100 |
| C | 100 | 100 | 100 | 100 | 100 |

B. Test against Botrytis cinerea on lettuce leaves

Lettuce leaves were placed in Petrie dishes and were contaminated with pieces of filter paper enriched with a suspension of conidies and the leaves were sprayed with 1 ml of a solution of the test product onto the surface of the Petrie dishes having 100 mm diameter. For inoculation, a suspension of 100,000 conidies per ml of carrot juice was used and the contamination was effected on 4 points of each leaf with confetti impregnated with the conidies suspension. 5 leaves were used for each concentration and after storage for 5 days at 15° C, readings were taken at each point of attack and the results are expressed in Table 2 as percent of efficacy.

TABLE 2

| Compound | Concentration in ppm | | | |
|---|---|---|---|---|
| | 125 | 62.5 | 31.2 | 15.6 |
| A | 100 | 100 | 100 | 50 |
| B | 30 | 50 | 20 | — |
| C | 95 | 70 | 45 | 25 |

C. Test against Fusarium roseum 5 ml of a suspension of the test product and spores of Fusarium roseum placed on cellulose pellets were added to 45 ml of a gelose nutritive media and after 7 days of growth, the average diameter of the colonies was compared to the untreated controls. The results of Table 3 are expressed as percent of efficacy.

TABLE 3

| Compound | Concentration in ppm | | | | |
|---|---|---|---|---|---|
| | 40 | 20 | 10 | 5 | 1 |
| A | 100 | 100 | 100 | 90 | 20 |
| B | 100 | 100 | 100 | 80 | 0 |
| C | 100 | 40 | 80 | 40 | 40 |

D. Fungicidal activity against Phytophtora infestans

St. Pierre tomato leaves were kept alive and treated by inoculation by depositing drops of a conidies suspension. The leaves were then sprayed with the active compound at dosages of 1000, 500, 250 and 125 ppm at a rate of 0.5 ml per container with a diameter of 100 mm. The leaves were contaminated with a suspension of Phytophtora infestans in sterile water containing 100,000 conidies per ml at 4 different points of the leave and with 5 leaves for each concentration. After storage for 5 days at 18° C, the mildew spots appearing at the points of inoculation were counted and the results are reported in Table 4 as the percentage of efficacy.

TABLE 4

| Compound | Concentration in ppm | | | |
|---|---|---|---|---|
| | 1000 | 500 | 250 | 125 |
| A | 60 | 30 | 30 | 0 |
| B | 70 | 45 | 40 | 30 |
| C | 55 | 10 | 5 | 0 |

E. Test against *Erysiphe polygoni*

Cotyledonous leaves of cucumbers treated with the test product were contaminated with pieces of filter paper with spores of Erysiphe polygoni. Treatment was effected by spraying the cotyledonous leaves of cucumbers in pots with 1 ml per surface of pot with a 11 cm diameter. The spore suspension was made of sterile water containing 100,000 conidies per ml. 3 pots of 4 to 5 plants each were used for each concentration and the pots were stored at 20° C for 12 days. The degree of attack was noted to permit to show the activity. The results of Table 5 are expressed in percent of efficacy.

TABLE 5

| Compound | Concentration in ppm | | | | |
|---|---|---|---|---|---|
| | 750 | 375 | 187.5 | 93.7 | 46.8 |
| A | 100 | 30 | 100 | 92 | 92 |
| B | 100 | 100 | 100 | 5 | 17 |
| C | 100 | 100 | 17 | — | — |

The results of Tables 1 to 5 show that compounds A, B and C possess interesting fungicidal activity against the organisms tested.

Various modifications of the products and processes of the invention may be made without departing from the spirit or scope thereof and it should be understood that the invention is intended to be limited only as defined in the appended claims.

We claim:

1. A method of killing fungi comprising contacting fungi with a fungicidally effective amount of at least one active compound of the formula

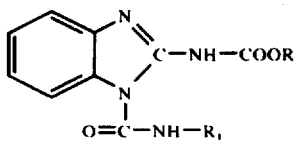

wherein R is alkyl of 1 to 2 carbon atoms and $R_1$ is selected from the group consisting of tetrahydrofurfuryl, pyranyl, dihydropyranyl, tetrahydropyranyl and tetrahydrofuranyl.

2. The method of claim 1 wherein the active compound is methyl 1-(4'-tetrahydropyranyl)-carbamoyl-2-benzimidazolyl-carbamate.

3. The method of claim 1 wherein the active compound is methyl 1-(2'-tetrahydropyranyl)-carbamoyl-2-benzimidazolyl-carbamate.

4. The method of claim 1 wherein the active compound is methyl 1-[3'-(5',6'-dihydropyranyl)]-carbamoyl-2-benzimidazolyl-carbamate.

5. The method of claim 1 wherein the compound is methyl 1-(2'-tetrahydrofurfuryl)-carbamoyl-2-benzimidazolyl-carbamate.

6. A fungicidal composition comprising a fungicidally effective amount of at least one compound of the formula

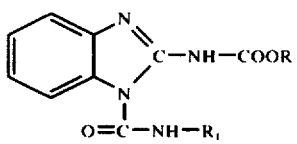

wherein R is alkyl of 1 to 2 carbon atoms and $R_1$ is selected from the group consisting of tetrahydrofurfuryl, pyranyl, dihydropyranyl, tetrahydropyranyl and tetranydrofuranyl and a carrier.

* * * * *